Reissued Sept. 25, 1923.

Re. 15,691

UNITED STATES PATENT OFFICE.

CARL PFANSTIEHL, OF HIGHLAND PARK, ILLINOIS, ASSIGNOR TO SPECIAL CHEMICALS COMPANY, OF HIGHLAND PARK, ILLINOIS, A CORPORATION OF ILLINOIS.

TOOTH-CLEANING PREPARATION.

No Drawing. Original No. 1,445,351, dated February 13, 1923, Serial No. 504,144, filed September 29, 1921. Application for reissue filed August 16, 1923. Serial No. 657,833.

*To all whom it may concern:*

Be it known that I, CARL PFANSTIEHL, a citizen of the United States, residing at Highland Park, in the county of Lake and State of Illinois, have invented a new and useful Improvement in Tooth-Cleaning Preparations, of which the following is a specification.

The present invention relates to improvements in preparations for cleansing teeth, root canals, and the like, and in general for use in oral hygiene and prophylaxis.

It has now been discovered that galactonic lactone is highly efficacious as a solvent for the organic binder or matrix of tartar, and, by a large number of experiments under my direction, it has been found that this material is without action upon the enamel of the teeth and that it exercises a stimulating action upon the gums. I have discovered that other members of the same class of compounds (which may be designated as potential acids in that they tend to form the corresponding acids in aqueous solution until an equilibrium between the potential acid and the corresponding acid is reached), of which the lactones of the sugar acids and particularly the lactones of the hexonic acids are examples, possess the same properties. Other suitable compounds of this class are, for example, mannonic lactone and gluconic lactone.

I have discovered that when these lactones are incorporated in pastes, powders and like compositions of the character hitherto known for general use as tooth-cleaning preparations, the lactone rapidly loses its activity and in many cases forms hard cement-like masses. These deleterious effects take place even when no water is employed as such in the vehicle in the case of pastes and they likewise occur in the case of powders containing the customary abradents and flavoring constituents, with or without saponaceous constituents.

In accordance with the present invention a substantially permanently active preparation containing the lactone may be prepared by intimately admixing the lactone with fillers which have been substantially completely dehydrated and in the case of a paste, employing a vehicle which is substantially anhydrous. The following examples illustrate the present invention.

Precipitated chalk, which normally contains up to 5% of moisture, is dried in a vacuum oven until substantially anhydrous.

Suitable flavoring substances, such as oil of eucalyptus, oil of wintergreen, thymol, saccharine, etc., are incorporated into it. 2 to 10% of a lactone of a sugar acid, for example, galactonic or mannonic lactone, is then added and thoroughly admixed. The powdered preparation may be employed as such, or may be formed into a paste by means of an anhydrous massing fluid, preferably comprising anhydrous glycerol (containing not more than 2% moisture) with or without absolute alcohol. Glycerol alone or equal parts of glycerol and alcohol may suitably be employed, the proportion of massing fluid and solids being equal in the above case. A small proportion, say 1 to 2% of gelatine may be dissolved in the vehicle, if desired.

If desired, other fillers may be substituted in whole or in part for the chalk. Thus tricalcium phosphate (previously dehydrated) or other inert substance such as kieselguhr may be substituted in the filler in whole or in part for chalk, or soap powder or saponin may be added. Soap powder, which ordinarily contains 10% or more moisture, must be heated in a vacuum oven to substantially complete freedom from water before use. When the soap is employed in the case of a paste the proportion of vehicle is reduced, and the proportion of alcohol to glycerine in the vehicle may likewise be reduced. The proportion of lactone to total solids is preferably between 2 and 10%.

The term anhydrous, as used herein, indicates the absence of water in a condition and in amount such as to cause loss of reactivity of the lactone employed or reaction between the products formed from it and a reactive filler.

I claim:

1. In a tooth cleaning compound, a substantially anhydrous filler and a lactone of a sugar acid.

2. In a tooth cleaning paste, a substantially anhydrous filler, a substantially anhydrous massing vehicle and a lactone of a sugar acid.

3. In a tooth cleaning compound, a substantially anhydrous filler comprising precipitated chalk, and galactonic lactone.

4. In a tooth cleaning paste, a substantially anhydrous filler comprising precipitated chalk, anhydrous glycerine, absolute alcohol and galactonic lactone.

5. In a tooth cleaning compound, a substantially anhydrous filler and galactonic lactone to the amount of 2 to 10% of the total solids.

6. In a tooth cleaning paste, a substantially anhydrous filler, a substantially anhydrous massing vehicle and galactonic lactone to the amount of 2 to 10% of the total solids.

7. In a tooth cleaning paste, a substantially anhydrous filler, a substantially anhydrous massing vehicle and a lactone of a sugar acid to the amount of 2 to 10% of the total solids.

CARL PFANSTIEHL.